United States Patent [19]

Fiecchi

[11] 4,057,686

[45] Nov. 8, 1977

[54] SULPHONIC ACID SALTS OF S-ADENOSILMETHIONINE

[75] Inventor: Alberto Fiecchi, Milan, Italy

[73] Assignee: Bioresearch Limited, Milan, Italy

[21] Appl. No.: 594,601

[22] Filed: July 9, 1975

[30] Foreign Application Priority Data

July 12, 1974 Italy .................. 25128/74

[51] Int. Cl.² .......................... C07H 19/16
[52] U.S. Cl. ..................... 536/26; 424/180
[58] Field of Search ............... 260/253, 252; 536/26

[56] References Cited

U.S. PATENT DOCUMENTS

| | | | |
|---|---|---|---|
| 3,707,536 | 12/1972 | Haid et al. | 536/26 |
| 3,893,999 | 7/1975 | Fiecchi | 536/26 |
| 3,954,726 | 5/1976 | Fiecchi | 536/26 |

Primary Examiner—Paul M. Coughlan, Jr.
Attorney, Agent, or Firm—Stevens, Davis, Miller & Mosher

[57] ABSTRACT

Stable salts of S-adenosil-L-methionine (SAM) with sulphonic acids chosen from the group consisting of methanesulphonic, ethanesulphonic, 1-n-dodecanesulphonic, 1-n-octadecanesulphonic, 2-chloroethanesulphonic, 2-bromoethanesulphonic, 2-hydroxyethanesulphonic, 3-hydroxypropanesulphonic, d-, 1, -d, 1-10-camphorsulphonic, d-, 1-, d, 1-3-bromocamphor-10-sulphonic, cysteic, benzenesulphonic, p-chlorobenzenesulphonic, 2-mesitylbenzenesulphonic, 4-biphenylsulphonic, 1-naphthalenesulphonic, 2-naphthalenesulphonic, 5-sulphosalicylic, p-acetylbenzenesulphonic, 1,2-ethanedisulphonic, o-benzenedisulphonic and chondroitinesulphuric acids, and double salts of said acids with sulphuric acid.

23 Claims, No Drawings

SULPHONIC ACID SALTS OF S-ADENOSILMETHIONINE

This invention relates to new salts of S-adenosilmethionine and organic sulphonic acids, and mixed salts of these latter, sulphuric acid and S-adenosilmethionine, the process for the preparation thereof and therapeutic compositions containing them. More precisely, the present invention relates to new extremely stable salts of S-Adenosil-L-Methionine (SAM), to a process for their simple and economical preparation on an industrial scale and new pharmaceutical compositions which contain them as their active principle, for use in numerous fields of human therapy. SAM is notably a product of natural origin, found in all living organism from bacteria to plants, from single cell organisms to superior mammals including man, the structure of which has been known for some time and is identified by the following formula:

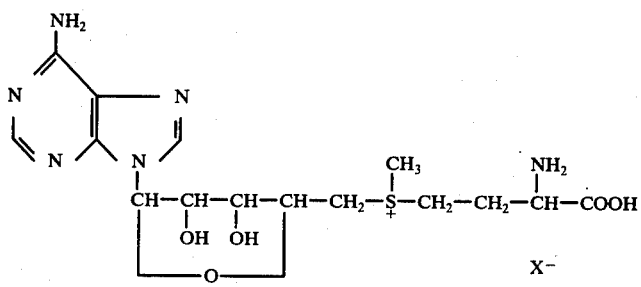

in which X is a generic anion.

In living organisms SAM is formed by the intervention of enzymes (S-adenosilmethioninsynthetasis or S-adenosiltransferasis) in the cytoplasmatic ambit starting from methionine assumed with the nutriments or from ATP present as energy reserve in every living cell.

It has also been known for some time that SAM is a product of fundamental importance in a large number of biological reactions of enzymatic transmethylation, because of which it has always been considered a very important reagent in biochemistry. The big problem with this substance has however always been its extreme instability at or above ambient temperatures, and its methods of production which are laborious and cannot easily be carried out on an industrial scale.

In recent years, research directed towards stabilising SAM to such an extent as to make its use possible in the field of biological research has been directed towards the preparation of salts which are stable under normal temperature and humidity conditions.

In this way the chloride and sulphate of SAM have been prepared, but they are of use only as reagents in biochemistry and only for short times, because even in the dry state their stability is limited in time at low temperatures. Furthermore their preparation processes are useful for the production of small quantities, but certainly not for production on an industrial scale. We have now completely unexpectedly found new salts of SAM which are indefinitely stable with time at temperatures up to 45° C, and which can be prepared by a new process easily carried out economically on an industrial scale, giving high yields. These salts have proved surprisingly to possess strong curative power in many fields of human therapy, often apparently without correlation between them.

The new salts according to the present invention are double salts of SAM with sulphonic acids, corresponding to the formula SAM. 4RSO$_3$H, in which RSO$_3$H is one of the following acids:
methanesulphonic, CH$_3$SO$_3$H; ethanesulphonic, C$_2$H$_5$SO$_3$H; n-dodecanesulphonic, C$_{12}$H$_{25}$SO$_3$H; 1-octadecanesulphonic, C$_{18}$H$_{37}$SO$_3$H; 2-chloroethanesulphonic, Cl C$_2$H$_4$SO$_3$H; 2-bromoethanesulphonic, BrC$_2$H$_4$SO$_3$H; 2-hydroxyethanesulphonic, HOC$_2$H$_4$SO$_3$H; 3-hydroxypropanesulphonic, HOC$_3$H$_6$SO$_3$H; d,1-10-camphor-sulphonic, C$_{10}$H$_{17}$OSO$_3$H; d-, 1-, d,1,-3-bromocamphor-10-sulphonic, C$_{10}$H$_{16}$BrOSO$_3$H; cysteic, C$_3$H$_6$NSO$_3$H. The present invention also relates to salts of SAM with sulphonic acids corresponding to the general formula SAM.3RSO$_3$H in which RSO$_3$H is one of the following acids:
benzenesulphonic, C$_6$H$_5$SO$_3$H; p-chloro-benzenesulphonic, Cl C$_6$H$_4$SO$_3$H; 2-mesitylbenzenesulphonic, (CH$_3$)$_3$C$_6$H$_2$SO$_3$H; 4-biphenylsulphonic, C$_{12}$H$_{10}$SO$_3$H; 1-naphthalenesulphonic, C$_{10}$H$_7$SO$_3$H; 2-naphthalenesulphonic, C$_{10}$H$_7$SO$_3$H; 5-sulphosalicylic, C$_7$H$_5$O$_3$SO$_3$H; p-acetylbenzenesulphonic, C$_8$H$_7$OSO$_3$H. The present invention also relates to salts of SAM with the following acids: 1,2-ethanedisulphonic, corresponding to the formula SAM.2 C$_2$H$_4$(SO$_3$H)$_2$; o-benzenedisulphonic, corresponding to the formula SAM.1,5 C$_6$H$_4$(SO$_3$H)$_2$ and chondroitinesulphuric corresponding to the formula SAM. 4C$_{14}$H$_{21}$NO$_{14}$S. The present invention also relates to the following double salts between sulphuric acid and any one of the aforementioned sulphonic acids, corresponding to the general formulas:

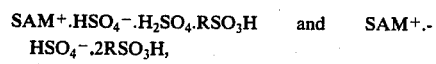

in which RSO$_3$H indicates any one of the aforementioned sulphonic acids or represents the equivalent acid in the case of ethanedisulphonic, o-benzenedisulphonic or chondroitinesulphuric acids.

The great technical progress achieved by these new salts is their stability with time at 45° in the dry state.

The SAM content of all acids according to the present invention remains unchanged even after 360 days at 45° in the dry state. The two most stable salts of SAM known up to the present time, the chloride and sulphate, show a SAM content after 30 days at 45° in the dry state of 20% and 50% respectively; after 60 days the former has completely decomposed, while the sulphate contains only 5% of the initial SAM.

The process for preparing the new salts according to the invention comprises essentially the following stages:
a. preparation of a solution rich in SAM either by extraction from natural substances which contain it or by enzymatic synthesis from adenosin triphosphate (ATP) and methionine.

b. precipitation of the SAM present in the filtered aqueous solution by a saturated aqueous solution of picrolonic acid or by solutions of the same acid in organic solvents soluble in water such as methyl, ethyl, propyl, isopropyl, n-butyl, or isobutyl alcohols; or acetone, methylethylketone, methylisobutylketone, ethyl acetate, tetrahydrofuran, 2-methoxyethanol, 2-ethoxyethanol, dioxan or dimethylformamide.

c. dissolving the filtered precipitate in a solution of one of the aforementioned acids in an alcohol such as methanol, ethanol, 1-propanol, 2-propanol, 1-butanol, 2-butanol, sec-butanol or 2-methoxyethanol or 2-ethoxyethanol.

d. adding to the solution an organic solvent miscible with the alcohol used, such as benzene, toluene, diethyl ether, diisopropyl ether, acetone, methylethylketone, methylisobutylketone, ethyl or methyl acetate, tetrahydrofuran or chloroform.

e. separating the organic liquid and redissolving the precipitate in a solution of the acid used in stage (c) in one of the alcohol solvents of stage (c), and treating the solution with decolorising carbon.

f. adding to the solution an organic solvent able to precipitate the pure SAM salt in a well crystalline and easily filterable form, chosen from one of those indicated in stage (d).

The first two stages of the process for obtaining double salts with sulphuric acid are identical, while the subsequent stages may be carried out as follows:

c'. dissolving the filtered precipitate in a mixture consisting of equal parts by volume of a solvent partially miscible with water such as methylethylketone, methylisobutylketone, n-butanol or isobutanol and an aqueous solution of equal normality of one of the aforementioned sulphonic acids and sulphuric acid.

d'. separating the organic layer and adding to the aqueous solution a ketone or alcoholic solvent completely soluble in water.

e'. redissolving the precipitate in a 10–20% solution of the acid used in stage (c') in one of the alcoholic solvents of stage (c) and treating the solution with decolorising charcoal.

f'. adding an organic solvent able to precipitate the pure SAM in a well crystalline and easily filterable form.

In accordance with one variation, the double salts are obtained by subjecting the simple salt obtained at the end of the aforementioned stage (d) to the following stages:

e''. redissolving the precipitate in an aqueous solution of equal normalities of sulphuric acid and the acid used in the previous stage (c) and treating the solution with decolorising carbon.

f''. adding an organic solvent able to precipitate the pure SAM salt in a well crystalline and easily filterable form.

As stated, stage (a) of the process can be carried out in different ways which are equally efficient for the purposes of obtaining a concentrated solution of SAM.

According to one alternative, yeast (Saccharomyces Cerevisiae, Torulopsis utilis, Candida utilis etc.), enriched in SAM by the addition of methionine under suitable conditions (Schlenk, Enzymologia 29, 283 (1965)), is treated with ethyl acetate and then with sulphuric acid having a normality between, 0.1 and 0.5, preferably 0.35 N, at ambient temperature, so as to cause lysis of the cells and the passage into solution of practically 100% of the SAM present.

Preferably quantities of water and acetate between 1/20 and 1/5 of the weight of the humid cells are used, and the treatment is protracted for a time between 15 and 45 minutes, preferably for 30 minutes.

Sulphuric acid is then added, and lysis is protracted for a time between one hour and two hours, preferably one hour and a half.

It should be noted that the lysis of the yeast cells conducted with a mixture of organic solvent and dilute sulphuric acid is much more convenient than that normally carried out with perchloric acid at ambient temperature, or with formic acid or acetic acid at 60° C and the like, in that not only does it take place at ambient temperature, which is very favourable to the stability of the SAM, but is conducted under such conditions that the solution can be easily filtered from the cellular residues, and does not contain any of the impurities which are present when the other lysant means are used, and which are difficult to eliminate with the known processes for preparing pure SAM.

According to a further alternative, the stage (a) is carried out by preparing the SAM by enzymatic synthesis, by the action of the enzyme ATP-methionine-adenosiltransferasis (E.C. 2.4.2.12) on an incubation mixture containing adenosiltriphosphate (ATP) and methionine.

The essential condition for the industrial execution of this method is that the enzyme is pure and is in a form which is easily isolated both from the initial incubation mixture and from the SAM produced.

The Applicant has discovered a process for purifying the enzyme ATP-methionine-adenosiltransferasis by chromatography by affinity, and a column reaction method, which enable the aforesaid objects to be attained.

The affinity chromatography of the specific enzyme according to the present invention is carried out by percolating a solution containing it, for example a raw extract of yeast or "*Escherichia coli*", through a column filled with a support solid to which a group which acts as a competitive inhibiter of the enzyme has been covalently bonded.

It has been surprisingly found that an excellent filling for such a purification column consists of an activated gel of polysaccharides to which L-lysine has been covalently bonded. The affinity of the specific enzyme for the lysine residue bonded to the solid matrix causes a delay in elution of the enzyme by the column, and it is thus possible to obtain separation from the other proteins in a very pure form.

However the separation of the enzyme from the eluate which contains it, for use in the subsequent enzymatic synthesis stage, has given completely unsatisfactory results because once separated, its stability diminished with time, and in addition after being used only once in the synthesis of the SAM, it was destroyed in the subsequent SAM isolation operations.

The applicant has found that excellent results are obtained instead by adsorbing the eluate containing the specific enzyme on a suitable support solid and carrying out the catalytic reaction between methionine and ATP in the column, leading to the formation of SAM.

A suitable solid support consists of a polysaccharide activated by a reagent suitable for bonding proteins to solid supports, such as cyanogen bromide.

By percolating a solution of ATP and methionine in a suitable buffer solution through the column, an eluate containing the SAM is obtained at the base of the column.

The stage (b) of the process enables the SAM to be separated in a state of high purity. In fact, in an acid environment the only compound precipitated by picrolonic acid is SAM, as is shown by thin layer chromatography in accordance with Anal. Biochem. 4, 16-28 (1971).

Picrolonic acid has thus an extremely and surprisingly selective action. The other precipitating agents added up to the present time, such as picric acid, Reinecke salt, or boric acid, give very impure precipitates which always require subsequent purification of the SAM by ion exchange column chromatography, a process which is extremely costly and difficult to carry out industrially.

It is also difficult to obtain the product with the necessary purity.

The use of aqueous solutions of picrolonic acid or solutions of this acid in the aforementioned organic solvents does not present particular problems, and is an operation which is carried out at ambient temperature.

Stage (c) is preferably carried out with solutions containing one of the aforementioned sulphonic acids in concentrations between 0.25 and 1.5 N, preferably 1N, and with one of the alcoholic solvents indicated.

The decomposition of the feed with the picrolonic acid of the SAM is complete, as the total dissolving of the solid shows. The stage (d) of the process is carried out by preferably using 4 to 10 volumes (with respect to the volume of the alcoholic solution) of a solvent chosen from the group comprising benzene, toluene, diethyl ether, diisopropyl ether, acetone, methylisobutylketone, methyl or ethyl acetate, or tetrahydrofuran. The stage (e) of the process forms with the subsequent stage (f) the final passage for obtaining the required SAM salt. This salt, originating from the previous stage (d), is redissolved in a solution of normality lying between 0.1 and 0.5 N, preferably 0.2 N, of the acid used in the previous stage (c) in a solvent chosen from the alcohols containing 1 to 4 carbon atoms, 2-methoxyethanol and 2-ethoxyethanol.

The subsequent stage (f) is carried out by preferably using 4 to 8 volume (with respect to the volume of the alcoholic solution) of an organic solvent chosen from the group comprising benzene, toluene, diethyl ether, diisopropyl ether, acetone, methylethylketone, methylisobutylketone, methyl or ethyl acetate, tetrahydrofuran and chloroform.

The simple SAM salts obtained in accordance with the present invention may be preserved in the dry state indefinitely, practically without alteration, as already stated.

The process discovered excludes water in all stages subsequent to precipitation with picrolonic acid, therefore ensuring the complete absence of minimal traces of impurities soluble in water.

Double salts of SAM with sulphuric acid and one of the sulphonic acids chosen from those stated in accordance with the first variation are obtained by preferably carrying out stage (c') of the process with aqueous solutions containing one of the aforementioned sulphonic acids and sulphuric acid in concentrations both between 0.05 and 0.2 N, preferably 0.1 N, in an organic solvent partially miscible with water such as methylethylketone or n-butanol. The use of the organic solvent enables the aqueous acid solutions to be very much reduced and practically eliminates all the picrolonic acid.

Stage (d') of the process is carried out by preferably using 4 to 8 volumes (with respect to the volume of the aqueous solution) of a solvent chosen from the group comprising acetone, methyl alcohol, ethyl alcohol and propyl alcohol.

It has also been surprisingly found that if in stage (e') the minimum quantity of alcohol necessary to dissolve the precipitate originating from stage (d') is used, the double salt $SAM^+.HSO_4^-.H_2SO_4.2R-SO_3H$ separates out in the subsequent precipitation stage (f').

If however a volume of alcohol equal to at least double the necessary volume is used in stage (e'), the double salt $SAM^+.HSO_4^-.H_2SO_4.R-SO_3H$ separates in the subsequent precipitation stage (f').

The use of intermediate quantities of alcohol leads to the formation of mixtures of the two salts.

$R-SO_3H$ indicates any one of the aforementioned sulphonic acids or the equivalent acid in the case of ethanedisulphonic acid or chondroitinesulphonic acid.

The final precipitation of one or other of the new salts according to the invention (stage f') requires the use of an organic solvent chosen from the group consisting of benzene, toluene, diethyl ether, diisopropyl ether, chloroform, acetone, methylethylketone, methylisobutylketone, methyl or ethyl acetate, isoamylalcohol or tetrahydrofuran.

As stated, the double salts of SAM obtained in accordance with the present invention may be preserved indefinitely in their dry state, practically without alteration.

The preparation of double salts of SAM with sulphuric acid and one of the aforementioned sulphonic salts using the second variation consists of redissolving (stage e'') the salt obtained in stage (d) in a solution of equal normalities, usually between 0.05 and 0.2 N and preferably 0.1 N, of sulphuric acid and the acid used in the previous stage (c) in one of the alcohols containing 1 to 4 carbon atoms or in 2-methoxyethanol or 2-ethoxyethanol.

It has also been surprisingly found that if in stage (e'') the minimum quantity of alcohol necessary to dissolve the precipitate originating from stage (d) is used, the double salt $SAM^+.HSO_4^-.H_2SO_4.2R-SO_3H$ (where $R-SO_3H$ indicates any one of the sulphonic acids or represents the equivalent acid of ethanedisulphonic acid or chondroitinesulphuric acid) separates in the subsequent precipitation stage (f'').

If however a volume of methanol equal to at least double the necessary minimum volume is used in stage (e''), the double salt $SAM^+.HSO_4^-.H_2SO_4.RSO_3H$ separates in the subsequent precipitation stage (f'').

The use of intermediate quantities of alcohol leads to the formation of mixtures of the two salts.

The final precipitation of one or other of the double salts (stage f'') requires the use of an organic solvent chosen from the group consisting of benzene, toluene, diethylether, diisopropylether, chloroform, alcohols with 4 and 5 carbon atoms, ethyl and methyl acetate, tetrahydrofuran, acetone, methylethylketone and methylisobutylketone.

The following examples illustrate the method of preparation of the new salts according to the invention, it being however understood that these examples are purely indicative and do not limit the invention.

EXAMPLE 1

To 90 kg of yeast enriched with SAM (6.88 g/kg) in accordance with Schlenk (Enzymologia 29, 283 (1965))

are added 11 l of ethyl acetate and 11 l of water at ambient temperature. After energetic agitation for 30 minutes, 50 l of 0.35 N sulphuric acid are added, continuing agitation for a further hour and a half. After filtering and washing with water, 140 l of solution are obtained containing 4.40 g/l of SAM, equal to 99.5% of that present in the starting material.

A solution of 2.3 kg of picrolonic acid in 25 liters of methylethylketone is added to the previous solution under agitation. After standing for one night, the precipitate is separated by centrifuging and washed with water.

The precipitate is dissolved under agitation at ambient temperature in 6.2 liters of a 1 N solution of methanesulphonic acid in methanol.

After filtering out traces of insoluble material, 50 liters of acetone are added to the solution. After complete sedimentation of the precipitate, the overlying solution is decanted and the insoluble residue is washed with a little acetone. The precipitate is dissolved in 25 l of a 0.25 N solution of methanesulphonic acid in methanol, decolorising carbon is added and the solution filtered. 125 l of methylisobutylketone are added to the filtrate. 1089 g of a well crystalline and easily filterable salt precipitate, soluble to more than 20% in water with the formation of a colourless solution is formed. The salt is only slightly soluble in common organic solvents. From thin layer chromatography in accordance with Anal. Biochem. 4, 16–28 (1971) the product is shown to be free from any impurity. The analytical data are given in Table 1 and agree with a compound of formula:

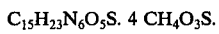
$C_{15}H_{23}N_6O_5S \cdot 4 CH_4O_3S.$

The new compound was also identified by the enzymatic method based on enzymatic methylation of nicotinamide and guanidinoacetic acid with SAM (G. L. Cantoni, J. Biol. Chem. 189, 745 (1951); G. De La Hoba, B. A. Jameison, S. H. Mudd and H. H. Richards, J. Am. Chem. Soc. 81, 3975 (1959)).

Repeating the process identically but using n-dodecanesulphonic and 1-n-octadecanesulphonic acids salts are obtained of the following formulas respectively:

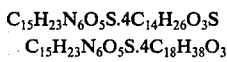
$C_{15}H_{23}N_6O_5S \cdot 4C_{14}H_{26}O_3S$ and
$C_{15}H_{23}N_6O_5S \cdot 4C_{18}H_{38}O_3S$ the analytical data of which is given in Table 1.

EXAMPLE 2

1.15 kg of picrolonic acid dissolved in 10 liters of isobutyl alcohol are added to 70 liters of solution originating from the lysis of yeast cells, obtained by using the same raw material and same method as Example 1.

After standing for one night, the precipitate formed is separated by centrifuging.

The precipitate is dissolved at ambient temperature under agitation in 3.1 liters of a 1 N solution of ethanesulphonic acid in ethanol.

After filtering out a small quantity of insoluble matter, 25 liters of diethyl ether are added to the solution. After standing, the mixture is filtered and the solid washed with a little ether.

The solid is dissolved in 12.5 liters of an 0.25 N solution of ethanesulphonic acid in ethanol, decolorising carbon is added and the mixture filtered. 63 liters of benzene are added to the filtrate.

585 g of salt are precipitated, and are filtered and dried. The compound is soluble in water to more than 20%, and is slightly soluble in common organic solvents. From thin layer chromatography as in Example 1, the compound is shown to be free from any impurity.

The analytical data is given in Table 1 and agrees with a product of formula:

$C_{15}H_{23}N_6O_5S \cdot 4C_2H_6O_3S.$

The new compound was also identified by the enzymatic method given in Example 1.

On repeating the process in an identical manner but using 2-bromoethanesulphonic and 2-chloroethanesulphonic acids, salts are obtained of the following formulas respectively:

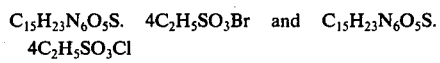
$C_{15}H_{23}N_6O_5S \cdot 4C_2H_5SO_3Br$ and $C_{15}H_{23}N_6O_5S \cdot 4C_2H_5SO_3Cl$ the analytical data of which is given in Table 1.

EXAMPLE 3

1.15 kg of picrolonic acid dissolved in 12 liters of n-butanol are added to 70 liters of solution originating from the lysis of yeast cells, obtained by the same lysis method and with the same raw material as in Example 1. After standing overnight, the precipitate is separated by centrifuging. The precipitate is dissolved at ambient temperature under agitation in 3.1 liters of a 1N solution of D,L-10-camphorsulphuric acid in 1-propanol.

25 liters of benzene are then added. The separated solid is dissolved in 12.5 liters of an 0.25N solution of camphorsulphuric acid in 1-propanol and after adding carbon and filtrating, 63 liters of acetone are added to the filtrate. 928 g of salt are obtained. The compound is soluble in water to more than 20% and is only slightly soluble in common organic solvents. From thin layer chromatography, the compound is shown to be free from any impurity.

The analytical data is given in Table 1 and agrees with a product of formula:

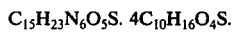
$C_{15}H_{23}N_6O_5S \cdot 4C_{10}H_{16}O_4S.$

The new compound was also identified by the enzymatic method given in Example 1.

On repeating the process in an identical manner but using d-3-camphor-10-sulphuric acid, a salt is obtained of formula:
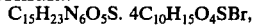
$C_{15}H_{23}N_6O_5S \cdot 4C_{10}H_{15}O_4SBr,$ the analytical data of which is given in Table 1.

EXAMPLE 4

Purification of the specfic enzyme 50 ml of Sepharose (polysaccharide produced by Pharmacia Fine Chemicals AB, Uppsala - Sweden) caked and suspended in water, are treated with cyanogen bromide in accordance with known methods for bonding substances containing amino groups to matrices consisting of polysaccharide gel. An excess of L-lysine is added to the gel so prepared. After the reaction, it is repeatedly washed with distilled water, with a pH 8.5 buffer mixture and with a pH 4.5 buffer mixture. The gel is then used for packing a column of diameter 1.5 cm and height 30 cm. A buffer mixture of 0.05 M triethanolamine and 0.01 M $H_2SO_4$ of pH 8.0 is passed through the column until complete equilibrium is obtained. 2 ml of yeast extract containing the specific enzyme, obtained by sonification or by homogenising with dry ice and possibly after enrichment with the specific enzyme, are depositated on the column. The column is then eluted with the same buffer mixture as used for equilibration, following the distribution of the proteins in the eluate by ultraviolet spectrophotometric measurements. Simultaneously the synthetasis activity is measured in the various fractions in accordance with J. A. Stekol, Methods in Enzymology, vol. 6, page 566 (1963). Those fractions displaying a relevant synthetasis activity are put together and the solution so obtained shows a specific activity at least twenty times greater than the raw extract. The enzyme can be further concentrated in this solution by the precipitation with salts, with organic solvents or in accordance with other known methods for concentrating protein solutions.

Preparation of SAM 30 ml of caked Sepharose gel are activated with cyanogen bromide or by any other known method for bonding proteins to polysaccharide gel matrices. 4 ml of a solution of the specific enzyme purified as above and containing about 100 mg of protein are added to the activated gel. The activated gel suspension and the enzyme solution are agitated at 4° C for 18 hours. The resin is washed with water. This wash liquid contains about 70% of the total enzymatic activity intially present in the solution of the specific enzyme. By incubating the Sepharose prepared as above by the aforementioned method for determining synthetasis activity, it is observed that approximately 20% of the total activity is bonded to the polysaccharide.

The Sepharose prepared as above is used for packing a column of diameter 1.5 cm and height 20 cm. A solution containing 0.675 M triethanolamine, 0.150 M magnesium sulphate, 0.05 M ATP, 0.05 M M-methionine and 0.01 M KCl is passed through the column at a speed of 5 ml per hour and at a temperature of 25°–27°. The eluate from the column analysed for SAM content shows that the conversion yield is 30%.

Preparation of SAM p-chlorobenzenesulphonate 103 ml of eluate containing 6 g/l of SAM are acidified with sulphuric acid until a pH of 3 is reached, and to this is added under agitation a solution of 2-3 g of picrolonic acid in 25 ml of methylethylketone.

After standing overnight the precipitate is filtered and washed with water.

The precipitate is redissolved in 6.2 ml of a 1N solution of p-chlorobenzenesulphonic acid in 2-methoxyethanol. 50 ml of toluene are then added. The separated solid is dissolved in 12.5 ml of an 0.25N solution of p-chlorobenzenesulphonic acid in 2-methoxyethanol and after adding carbon and filtering, 60 ml of chloroform are added to the filtrate.

1.43 g of salt are obtained. The compound is soluble in water to more than 20% and is only slightly soluble in common organic solvents.

From thin layer chromatography the salt is shown to be free from any impurity.

The analitical data is given in Table 1 and agree with a compound of formula:

$C_{15}H_{23}N_6O_5S . 3C_6H_5ClO_3S.$

The new compound was also identified by the enzymatic method described in Example 1.

On repeating the process in an identical manner but using p-acetylbenzenesulphonic, o-benzenedisulphonic, 4-biphenylsulphonic, 2-mesitylenesulphonic and 5-sulphosalicylic acid, salts are obtained having the following respective formulas:

$C_{15}H_{23}N_6O_5S . 3C_8H_8O_4S;$ $C_{15}H_{23}N_6O_5S . 1.5 C_6H_6O_6S_2;$ $C_{15}H_{23}N_6O_5S . 3C_{12}H_{10}O_3S;$ $C_{15}H_{23}N_6O_5S . 3C_9H_{12}O_3S;$ $C_{15}H_{23}N_6O_5S . 3C_7H_6O_6S$ the analytical data of which is given in Table 1.

EXAMPLE 5

The precipitate obtained after adding picrolonic acid to 70 liters of solution as in Example 1 is dissolved at ambiente temperature under agitation in 3.1 liters of a 1N solution of 1,2ethanedisulphonic acid in methanol.

25 liters of acetone are then added. The separated solid is dissolved in 12.5 liters of a 0.25N solution of 1,2 ethanedisulphonic acid in methanol and after adding carbon and filtering, 60 liters of methylisobutylketone are added to the filtrate. 546 g of salt are obtained. The compound is soluble to more than 20% in water and is only slightly soluble in common organic solvents.

From thin layer chromatography the compound is shown to be free from any impurity.

The analytical data is given in Table 1 and agrees with a product of formula:

$C_{15}H_{23}N_6O_5S . 2 C_2H_6O_6S_2.$

The new compound was also identified by the enzymatic method described in Example 1.

EXAMPLE 6

The precipitate obtained after adding picrolonic acid to 70 liters of solution as in Example 1 is dissolved at ambient temperature under agitation in 3.1 liters of a 1N solution of 2-hydroxyethanesulphonic acid in ethanol.

25 liters of methylisobutylketone are then added.

The separated solid is dissolved in 12.5 liters of an 0.25N solution of 2-hydroxyethanesulphonic acid in ethanol and after adding carbon and filtering, 80 liters of tetrahydrofuran are added to the filtrate.

632 g of salt are obtained. The compound is soluble in water to more than 20% and only slightly soluble in common organic solvents.

From thin layer chromatography the compound is found to be free from any impurity.

The analytical data is give in Table 1 and agrees with a product of formula:

$C_{15}H_{23}N_6 5S . 4 C_2H_6O_4S.$

The new compound was also identified by the enzymatic method described in Example 1.

On repeating the process in an identical manner but using 3-hydroxypropanesulphonic acid, a salt is obtained of formula:

$C_{15}H_{23}N_6O_5S . 4 C_3H_8O_4S$ the analytical data of which are given in Table 1.

EXAMPLE 7

The precipitate obtained after adding picrolonic acid to 70 liters of solution as in Example 1 is dissolved at ambient temperature under agitation in 3.1 liters of a 1N solution of 1-naphthalenesulphonic acid in methanol.

25 liters of methylethylketone are then added. The separated solid is dissolved in 12.5 liters of an 0.25 N solution of 1-naphthalenesulphonic acid in methanol, and after adding carbon and filtering, the filtrate is added to 70 liters of methylketone.

717 g of salt are obtained. The compound is soluble in water to more than 20% and is only slightly soluble in common organic solvents. From thin layer chromatography the compound is shown to be free from any impurity.

The analytic data is given in Table 1 and corresponds to a product of formula:

$C_{15}H_{23}N_6O_5S \cdot 3\ C_{10}H_8O_3S.$

The new compound was also identified by the enzymatic method described in Example 1.

EXAMPLE 8

The precipitate obtained after adding picrolonic acid to 70 liters of solution as in Example 1 is dissolved at ambient temperature under agitation in 3.1 liters of a 1N solution of 2-naphthalenesulphonic acid in 2-propanol.

25 liters of diisopropyl ether are then added. The separated solid is dissolved in 12.5 liters of an 0.25N solution of 2-naphthalenesulphonic acid in methanol, and after adding carbon and filtering, 70 liters of ethyl acetate are added to the filtrate. 710 g of salt are obtained. The compound is soluble in water to more than 20% and is only slightly soluble in common organic solvents.

From thin layer chromatography the compound is found to be free from any impurity.

The analytical data is given in Table 1 and corresponds to a product of formula:

$C_{15}H_{23}N_6S \cdot 3\ C_{10}H_8I_3S.$

The new compound was also identified by the enzymatic method described in Example 1.

EXAMPLE 9

The precipitate obtained after adding picrolonic acid to 70 liters of solution as in Example 1 is dissolved at ambient temperature under agitation in 3.1 liters of a 1N solution of benzene sulphonic acid in 2-butanol. 25 liters of diisopropyl ether are then added.

The separated solid is dissolved in 12.5 liters of a 0.25N solution of benzene sulphonic acid in methanol, and after adding carbon and filtering, 65 liters of ethyl acetate are added to the filtrate.

612 g of salt are obtained. The compound is soluble in water to more than 20% and is only slightly soluble in common organic solvents. From thin layer chromatography the compound is shown to be free from from any impurity.

The analytical data given in Table 1 agrees with a product of formula:

$C_{15}H_{23}N_6O_5S \cdot 3\ C_6H_6O_3S.$

The new compound was also identified by the enzymatic method described in Example 1.

EXAMPLE 10

The precipitate obtained after adding picrolonic acid to 103 ml of solution as in Example 4 is dissolved at ambient temperature under agitation in 6.2 ml of a 1N solution of chondroitinesulphuric acid in methanol. 50 ml of acetone are then added.

The separated solid is dissolved in 25 ml of a 0.25N solution of chondroitinesulphuric acid in methanol, and after adding carbon and filtering, 125 ml of methylisobutylketone are added to the filtrate.

3.27 g of salt are obtained. The compound is soluble in water to more than 20% and is only slightly soluble in common organic solvents. From thin layer chromatography it is shown to be free from any impurity. The analytical data are given in Table 1 and agree with a product of formula:

$C_{15}H_{23}N_6O_5S \cdot 4\ C_{14}H_{21}NO_{14}S.$

The new compound was also identified by the enzymatic method described in Example 1.

EXAMPLE 11

The precipitate obtained after adding picrolonic acid to 103 ml of solution as in Example 4 is dissolved at ambient temperature under agitation in 6.2 ml of a 1N solution of cysteic acid in 2-ethoxyethanol. 50 ml of dimethyl acetate are then added. The separated solid is dissolved in 25 ml of a 0.25N solution of cysteic acid in 2-ethoxyethanol, and after adding carbon and filtering, 125 ml of methyl acetate are added to the filtrate. 1.53 g of salt are obtained. The compound is soluble in water to more than 20% and is only slightly soluble in common organic solvents. From thin layer chromatography it is shown to be free from any impurity. The analytical data are given in Table 1 and agree with a product of formula:

$C_{15}H_{23}N_6O_5S \cdot 4\ C_3H_7NO_5S.$

The new compound was also identified by the enzymatic method described in Example 1.

EXAMPLE 12

Preparation of double salts of SAM with sulphuric acid and methanesulphonic acid.

103 ml of eluate containing 6 g/l of SAM obtained as in example 4 are acidified with $H_2SO_4$ until a pH of 3 is reached, and to this is added under agitation a solution of 2.3 g of picrolonic acid in 25 ml of methlethylketone (solvent a).

After standing for one night, the precipitate is filtered and washed with water. The precipitate is redissolved in 18 ml of an 0.1N solution of $H_2SO_4$ and methanesulphonic acid, and in 18 ml of methylethylketone (solvent a).

After agitation and standing, the organic layer is separated and the aqueous layer is shaken with a little methylethylketone to eliminate the last traces of picrolonic acid. After separating the water layer; decolorising carbon is added and the mixture is filtered. 16.5 ml of aqueous colorless solution are obtained, containing 33.8 gl of SAM, equal therefore to 90% of the SAM contained in the original solution. On analysis by thin layer chromatography, the solution is shown to contain only SAM.

16.5 ml of the solution are poured into 100 ml of acetone (solvent b).

After agitation and standing, the liquid is separated by decanting. The solid is dissolved in 6.6 g of a 15% solution of methanesulphonic acid in methanol (solvent c).

After adding decolorising carbon and filtering, the solution is poured into 25 ml of ethyl ether (solvent d). It is filtered after standing, and the well crystalline salt obtained weights 1.2 g and has the composition:

SAM+.HSO4−.H2SO4.2CH3SO3H.

Its analytical characteristics are given in Table 2.

On repeating the process in an identical manner but using sulphonic acids and solvents as indicated in Table 2, double salts are obtained as given in Table 2 with their analytical characteristics.

On repeating the process in an identical manner, but using 3.3 g of a 15% solution of methanesulphonic acid in methanol, the subsequent precipitation stage with 25 ml of ethyl ether (solvent d) gives 1.05 g of salt of composition:

SAM+.HSO4−.H2SO4H, the analytical characteristics of which are given in Table 3.

On repeating the process in an identical manner, but using sulphonic acids and solvents as indicated in the table, double salts are obtained, as given in Table 3 with their analytical characteristics.

EXAMPLE 13

Preparation of double salts of SAM with sulphuric acid and 2-hydroxyethanesulphonic acid The salt obtained from the first precipitation of SAM with 2-hydroxyethanesulphonic acid as in Example 6 is redissolved in 20 l of a solution of 0.1N of sulphuric acid and 0.1N of 2-hydroxyethanesulphonic acid in methanol (solvent a). It is filtered after adding decolourising charcoal, and 100 liters of methylisobutylketone (solvent b) are added to the filtrate.

The mixture is filtered after standing, and 587 g of salt of composition:

SAM+.HSO4−.H2SO4. 2C2H6O4S are obtained, having the analytica characteristics given in table 4.

On repeating the process in an identical manner, but using 10 liters of a solution of 0.1N of sulphuric acid and 0.1N of 2-hydroxyethanesulphonic acid in methanol (solvent a), the subsequent precipitation with methylisobutylketone (solvent b) gives 505 g of salt of composition:

SAM+.HSO4−.H2SO4.C2H6O4S, the analytical characteristics of which are given in Table 5. On repeating the process in an identical manner, but using simple SAM salts containing the anions given in table 5 and using the solvents indicated in Table 5, double salts are obtained, as indicated in Table 5 with their analytical characteristics. On repeating the process in an identical manner, but using 3.3 g of a 15% solution of p-toluensulphonic acid in methanol, the subsequent precipitation stage with 25 ml of ethyl ether gives 1.18 g of the salt SAM+.HSO4−.2 CH3C6H4SO3H, which has the same characteristics as those indicated for the product of Example 1.

TABLE 1

| ANION | BASIC FORMULA | %N found | %N calculated | % S found | % S calculated | % SAM found | % SAM calculated | max 260 nm E1% (6N H2SO4) |
|---|---|---|---|---|---|---|---|---|
| Methanesuphonate | C19H39N6O17S5 | 10.51 | 10.72 | 20.30 | 20.45 | 50.3 | 50.96 | 188 |
| Dodecanesulphonate | C71H127N6O17S5 | 5.55 | 5.61 | 10.91 | 10.70 | 26.37 | 26.68 | 98 |
| 1-octadecanesulphonate | C87H75N6O17S5 | 4.72 | 4.84 | 9.50 | 9.22 | 22.75 | 22.99 | 85 |
| Ethanesulphonate | C23H47N6O17S5 | 9.82 | 10.01 | 18.62 | 19.08 | 47.12 | 47.55 | 175 |
| 2-bromoethanesulphonate | C23H43N6O17S5Br4 | 7.35 | 7.28 | 13.68 | 13.88 | 34.67 | 34.58 | 127 |
| 2-chloroethanesulphonate | C23H43N6O17S5Cl4 | 8.58 | 8.59 | 16.31 | 16.39 | 40.89 | 40.84 | 151 |
| 10-camphorsulphonate | C55H87N6O21S5 | 5.97 | 6.33 | 11.53 | 12.06 | 29.52 | 30.06 | 111 |
| d-3-bromocamphor-10-sulphonate | C55H83N6O21S5Br4 | 5.14 | 5.11 | 9.81 | 9.75 | 24.02 | 24.30 | 89 |
| 2-hydroxyethanesulphonate | C23H47N6O21S5 | 8.91 | 9.30 | 17.25 | 17.73 | 43.82 | 44.19 | 163 |
| p-acetylbenzenesulphonate | C39H47N6O21S4 | 7.75 | 7.90 | | | | | |
| o-benzenedisulphonate | C24H32N6O14S4 | 11.10 | 11.08 | | | | | |
| 4-biphenylsulphonate | C51H53N6O14S4 | 7.49 | 7.63 | | | | | |
| 2-mesitylenesulphonate | C42H59N6O14S4 | 8.50 | 8.41 | | | | | |
| 5-sulphosalicylate | C36H41N6O23S4 | 7.99 | 7.97 | | | | | |
| 1,2-ethanedisulphonate | C19H35N6O17S5 | 10.31 | 10.78 | | | | | |
| 3-hydroxypropanesulphonate | C27H55N6O21S5 | 8.79 | 8.75 | | | | | |
| Cysteate | C27H51N10O25S5 | 12.50 | 13.02 | 12.01 | 12.05 | 37.31 | 37.54 | 138 |
| Chondroitinesulphate | C71H107N10O61S5 | 5.83 | 6.26 | | | | | |
| Benzenesulphonate | C33H41N6O14S4 | 9.34 | 9.62 | 16.76 | 16.90 | 52.75 | 52.64 | 194 |
| p-chlorobenzenesulphonate | C33H38N6O14S4Cl3 | 8.10 | 8.60 | 11.52 | 11.64 | 36.50 | 36.25 | 134 |
| 1-naphthalenesulphonate | C45H47N6O14S4 | 8.03 | 8.20 | | | | | |
| 2-naphthalenesulphonate | C45H47N6O14S4 | 7.83 | 8.20 | | | | | |

TABLE 1-continued

| | | | | |
|---|---|---|---|---|
| 12.67 | 12.82 | 40.11 | 39.94 | 147 |
| 12.01 | 12.17 | 37.68 | 37.90 | 140 |
| 20.03 | 20.55 | 50.68 | 51.22 | 189 |
| 16.55 | 16.70 | 41.32 | 41.61 | 153 |
| 14.68 | 14.90 | 36.92 | 37.12 | 137 |
| 6.84 | 7.17 | 17.21 | 17.86 | 66 |
| 14.22 | 14.67 | 45.18 | 45.69 | 169 |
| 12.72 | 13.12 | 40.53 | 40.87 | 151 |
| 12.03 | 12.52 | 38.73 | 39.00 | 144 |
| 11.95 | 12.52 | 38.52 | 39.00 | 144 |

TABLE 2

$SAM^+ \cdot HSO_4^- \cdot H_2SO_4 \cdot 2RSO_3H$

| ANION | SOLVENTS | | | |
|---|---|---|---|---|
| | a | b | c | d |
| Methanesulphonate | methylethylketone | acetone | methanol | ethyl ether |
| 10-camphorsulphonate | isobutanol | methanol | n-butanol | benzene |
| 2-bromoethane-sulphonate | n-butanol | ethanol | isobutanol | methylethyl-ketone |
| Chondroitinesulphate | methylisobutyl-ketone | acetone | methanol | ethyl acetate |
| p-chlorobenzene-sulphonate | methylethylketone | 1-propanol | 2-methoxy-ethanol | ethyl ether |
| 4-biphenylsulphonate | methylethylketone | methanol | 2-ethoxy-ethanol | diisopropyl-ether |

| BASIC FORMULA | calc. | found | calc. | found | calc. | found | $E_{1\,cm}^{1\%}$ at 260 nm ($H_2SO_4$ 6N) |
|---|---|---|---|---|---|---|---|
| $C_{17}H_{34}N_6O_{19}S_5$ | 10.68 | 10.81 | 20.37 | 20.02 | 50.77 | 51.10 | 187 |
| $C_{35}H_{58}N_6O_{21}S_5$ | 7.96 | 8.12 | 15.19 | 15.01 | 37.84 | 37.51 | 140 |
| $C_{19}H_{36}N_6O_{19}S_5Br_2$ | 8.64 | 8.75 | 16.48 | 16.10 | 41.06 | 41.30 | 151 |
| $C_{54}H_{68}N_8O_{41}S_5$ | 7.40 | 7.13 | 10.59 | 10.72 | 26.30 | 25.95 | 97 |
| $C_{27}H_{36}N_6O_{19}S_5Cl_2$ | 8.57 | 8.62 | 16.36 | 16.54 | 40.77 | 41.01 | 150 |
| $C_{39}H_{46}N_6O_{19}S_5$ | 7.91 | 8.12 | 15.08 | 15.20 | 37.57 | 37.82 | 139 |

TABLE 3

$Sam^+ \cdot HSO_4^- \cdot H_2SO_4 \cdot RSO_3H$

| ANION | SOLVENTS | | | |
|---|---|---|---|---|
| | a | b | c | d |
| Methanesulphonate | methylethylketone | acetone | methanol | ethyl ether |
| Dodecanesulphonate | methylisobutylketone | methanol | 2-methoxyethanol | ethyl ether |
| 1,2-ethanedisulphonate | n-butanol | ethanol | methanol | benzene |
| p-acetylbenzenesulphonate | isobutanol | methanol | n-butanol | toluene |
| 5-sulphosalicylate | methylisobutylketone | acetone | methanol | chloroform methylisobutylketone |

| BASIC FORMULA | % N calc. | found | % S calc. | found | % SAM calc. | found | $E_{1\,cm}^{1\%}$ at 260 nm ($H_2SO_4$ 6N) |
|---|---|---|---|---|---|---|---|
| $C_{16}H_{30}N_6O_{16}S_4$ | 12.7 | 11.95 | 18.57 | 18.71 | 57.83 | 57.62 | 213 |
| $C_{29}H_{52}N_6O_{16}S_4$ | 9.67 | 9.83 | 14.76 | 14.54 | 45.96 | 45.99 | 170 |
| $C_{16}H_{29}N_6O_{16}S_4$ | 11.17 | 11.01 | 17.04 | 17.25 | 53.07 | 53.22 | 196 |
| $C_{23}H_{34}N_6O_{17}S_4$ | 10.16 | 10.28 | 15.51 | 15.08 | 48.31 | 48.06 | 178 |
| $C_{28}H_{38}N_6O_{16}S_4$ | 9.97 | 9.65 | 15.21 | 15.37 | 47.39 | 47.11 | 175 |
| $C_{22}H_{32}N_6O_{19}S_4$ | 10.34 | 10.08 | 15.78 | 15.45 | 49.19 | 49.00 | 181 |

TABLE 4

$SAM^+ \cdot HSO_4^- \cdot H_2SO_4 \cdot 2RSO_3H$

| ANION | SOLVENTS | | |
|---|---|---|---|
| | a | b | |
| 2-hydroxyethanesulphonate | methanol | methylisobutylketone | $C_{19}H_{38}N_6O_{21}S_5$ |
| Ethanesulphonate | 2-methoxyethanol | acetone | $C_{19}H_{38}N_6O_{19}S_5$ |
| Cysteate | isopropanol | tetrahydrofuran | $C_{21}H_{40}N_8O_{23}S_5$ |
| 1-octadecanesulphonate | 2-ethoxyethanol | methyl acetate | $C_{51}H_{102}N_6O_{19}S_5$ |
| 2-chloroethanesulphonate | ethanol | chloroform | $C_{19}H_{36}N_6O_{19}S_5Cl_2$ |
| 2-naphthalenesulphonate | methanol | ethyl ether | $C_{35}H_{42}N_6O_{19}S_5$ |

| % N calc. | found | % S calc. | found | % SAM calc. | found | $E_{1\,cm}^{1\%}$ at 260 nm ($H_2SO_4$ 6N) |
|---|---|---|---|---|---|---|
| 10.02 | 10.15 | 19.11 | 19.23 | 47.62 | 47.43 | 176 |
| 10.31 | 10.01 | 19.67 | 19.35 | 49.02 | 49.28 | 181 |
| 12.01 | 12.26 | 17.18 | 17.02 | 42.82 | 42.55 | 158 |
| 6.65 | 6.40 | 12.68 | 12.49 | 31.61 | 31.29 | 117 |
| 9.51 | 9.38 | 18.14 | 18.32 | 45.20 | 45.36 | 167 |

TABLE 4-continued

| 8.30 | 8.07 | 15.84 | 15.64 | 39.47 | 39.50 | 146 |
|------|------|-------|-------|-------|-------|-----|

TABLE 5

SAM+ . HSO$_4^-$ . RSO$_3$H

| ANION | SOLVENTS a | b | BASIC FORMULA |
|---|---|---|---|
| 2-hydroxyethanesulphonate | methanol | methylisobutylketone | C$_{17}$H$_{32}$N$_6$O$_{17}$S$_4$ |
| 3-hydroxypropanesulphonate | 2-ethoxy-ethanol | ethyl ether | C$_{18}$H$_{34}$N$_6$O$_{17}$S$_4$ |
| d-3-bromocamphor-10-sulphonate | n-butanol | chloroform | C$_{25}$H$_{41}$N$_6$O$_{17}$S$_4$Br |
| 1-naphthalenesulphonate | ethanol | ethyl ether | C$_{25}$H$_{34}$N$_6$O$_{16}$S$_4$ |
| Benzenesulphonate | ethanol | methylisobutyl-ketone | C$_{21}$H$_{32}$N$_6$O$_{16}$S$_4$ |
| o-benzenedisulphonate | 2-methoxy-ethanol | benzene | C$_{18}$H$_{29}$N$_6$O$_{16}$S$_4$ |

| % N calc. | found | % S calc. | found | % SAM calc. | found | $E_{1\,cm}^{1\%}$ at 260 nm (H$_2$SO$_4$ 6N) |
|---|---|---|---|---|---|---|
| 11.66 | 11.45 | 17.79 | 17.95 | 55.42 | 55.15 | 204 |
| 11.44 | 11.62 | 17.45 | 17.01 | 54.36 | 54.30 | 201 |
| 9.28 | 9.08 | 14.16 | 14.20 | 44.10 | 43.91 | 163 |
| 10.47 | 10.57 | 15.99 | 16.12 | 49.75 | 49.62 | 183 |
| 11.16 | 11.22 | 17.03 | 16.95 | 53.06 | 53.15 | 196 |
| 11.78 | 11.53 | 17.97 | 17.62 | 55.97 | 55.65 | 206 |

For some years it has been known from biochemical research that SAM is the only specific donor of methyls in living organisms for the biochemical reactions of transfer of the CH$_3$ group, which are fundamental reactions in the lipidic, protidic and glucidic metabolism.

By way of example we give below some of the most important SAM-dependent transmethylation reactions:

a. N-transmethylation: adenine, carnitine, carnosine, creatine, 2,6-diaminopurine, adrenaline, guanine, hordenine, N'-nicotinamide, phosphatidilcoline, ricinine;

b. O-transmethylation: N-acetylserotonine, dopamine, epinine, d-adrenaline, 1-adrenaline, ergosterol, 1-noradrenaline, pectine, ubiquinone;

c. S-transmethylation: 2,3-dimercaptopropanol, H$_2$S, methionine, methylmercaptan, S-mercaptopropionic acid, S-mercaptoethanol, thiopyrimidine, thiouracyl;

d. C-transmethylation: cytosine, thymine.

This means, referring in particular to the human organism, that SAM acts in the following metabolic processes:

biosynthesis of choline; biosynthesis of phosphatidylcoline; activity of enzymes which require SH groups; metabolism of catecholamines; metabolism of biogene centroencephalic amines; metabolism of serotinine; metabolism of histamine; metabolism of vitamin B12 and folic acid; metabolsim of creatine; metabolism of myosine; metabolism of histones; metabolism of RNA; metabolism of DNA; metabolism of protein substances; metabolism of some hormones of cyclopentane perhydrophenantrenic nucleus, the main ones of which are the estrogens; metabolism of triglycerides.

It has also been known for some time that SAM, once demethylated by the methyltransferasic enzymes, is transformed into S-adenosilhomocysteine (SAO) which is an indirect donor of hydrosulphide groups and hence has a determining importance in the metabolism of all compounds which require SH groups for carrying out their biological activity.

Particularly important among these are some thioenzymes and the sulphurated amine acids.

SAO in its turn is decarboxylated in the organism, and the decarboxylated product is the principal donor of the aminopropyl group, indispensable — according to the most recent biochemical knowledge — for the biosynthesis of polyamines. The process is catalysed by various enzymes, including the specific aminopropyltransferasis.

Summarising we may say that it is known that SAM in the human organism is closely connected with all biochemical reactions of:

A — transmethylation (specific yielding of the CH$_3$ group)

B — transsulphuration (specific yielding of the SH group)

C — transaminopropylation (specific yielding of the aminopropyl group).

The sum of this knowledge could lead one to think that SAM could have some therapeutic action in the treatment of pathological states linked with the shortage or other deficiency conditions in the organism with respect to some of the many products mentioned above.

However the extreme instability of SAM and the lack, up to the present time, of any method for making it stable for sufficient times under normal ambient conditions has prevented this product from being given any pharmacological or clinical tests and hence has prevented any practical use being found for it in the field of human therapy.

Only after the preparation of the new SAM salts according to the present invention, salts which are practically indefinitely stable at ambient temperature, has it been possible to carry out a systematic pharmacological and clinical study which has led to the discovery for the new salts of therapeutic properties completely suprising in their quality and intensity.

From the enormous quantity of pharmacological and clinical data collected for this new product, we give hereinafter only some elements sufficient to clearly indicate the experts of the art the essential characteristics of the new product and its main uses in human therapy.

For simplicity hereinafter we shall indicate simply by "SAM salt" the new salts according to the invention, because of their absolute identical use.

In the pharmacological and clinical data, the salt administered is always indicated generically by SAM and the quantity of salt administered is expressed in terms of quantity of SAM contained in it, so that it is clear that the data refer identically to the one or other salt according to the invention.

TOXICITY

The SAM salts according to the invention have proved absolutely free from acute toxicity, chronic toxicity, local intolerance of secondary effects.

In particular, the $DL_{50}$ in the mouse in greater than 2.5 g/kg/os and 1.00 g/kg/i.p.

The tolerability and chronic toxicity tests were carried out on rats of the Wistar and Sprague-Dowley stock administering for 12 months 4–8 mg/kg per day of product: at the end of the treatment the various organs and apparatus showed no pathological alteration.

The teratogenesis tests were carried out on rabbits and rats: even with the administration of massive doses of SAM, approximately 10 times the maximum therapeutical doses, no teratogenic actions were encountered or any malformations in the embryons or terminal feti.

The addition of doses up to 0.05–0.10 mg/ml of product in surviving cultures of human lymphocytes or hepatic mouse cells does not produce any change in the blasticising index for the cellular elements.

The intravenous administration of doses up to 16 mg/kg does not produce any pyrogenic manifestation in the rabbit.

The venous administration in the rabbit and cat of 16 mg/kg doses does not cause any change in the carotid pressure, the cardiac and respiratory frequency or the electrocardiac trace. The local tolerability of the intramuscular injection, even after administrations repeated over 180 days, and of the intravenous injection in the marginal vein of the auricular pavilion of the rabbit, is excellent.

In man, in young volunteer healthy subjects of both sexes subjected to administration by the rapid intravenous method or by phleboclysis of doses of SAM equal to 5–150 mg (average weight 70 kg), the simultaneous examination of the minimum and maximum pressure and of the pulse and respiratory frequency at 1,5,15,20,30,60 minutes and at 2,3,6,8,10,12,24 hours from the end of administration does not show any variation from normal values. The electrocardiograph trace does not show any variation in the PQ interval, in the ST section, nor any appearance of extrasistol or other alterations at 30", 1', 2', 3', 5', 10' and 20' from administration.

In the hemopoietic apparatus and in the hepatic and renal operation there were no variations from normal which were statistically significant.

PHARMACOLOGY

We would repeat that each time we speak hereinafter of the administration of SAM, we mean that any one of the simple or double salts according to the invention has been administered, as their activity is entirely equivalent. In order to obtain a single reference parameter, reference is always made to the SAM content of the various salts.

In order to indicatively determine how SAM is distributed in the tissues, S-Adenosilmethionine (Methyl $C^{14}$) was prepared. The distribution of this product in rats was studied by administering a dose of 4.2 mg/kg/e.v. equal to approxymately 10 μci of radioactive product. The specific activity of the product was 58 mCi/m moles.

Parallel with this, an autoradiographic study was made on the mouse.

The results of these two experiments show that SAM is distributed very rapidly to all the tissues.

We given by way of example a part of the data relative to some of the organs considered:
Distribution of SAM in some rat tissues.
The values are expressed as μgr/gr.

| Tissue | 15' | 1 h | 4 h | 8 h | 24 h |
|---|---|---|---|---|---|
| Liver | 1.7 | 3.0 | 5.5 | 5.6 | 5.7 |
| Suprarenal glands | 1.9 | 3.4 | 4.8 | 4.5 | 4.4 |
| Spleen | 1.3 | 1.2 | 3.5 | 2.6 | 2.8 |
| Hypophysis | 2.3 | 2.5 | 8.0 | 4.5 | 4.2 |
| Hypothalamus | 0.3 | 0.65 | 1.0 | 1.3 | 1.3 |
| Rind | 0.25 | 0.45 | 0.75 | 8.5 | 9.4 |
| Plasma | 7.5 | 2.1 | 2.3 | 2.0 | 1.1 |

It was consequently deduced that the new salts according to the present invention donate the $CH_3$ group to all the tissues provided with methyltransferasis activity. In other words the capacity of the new products according to the invention to electively localise themselves in all the organs provided with methyltransferasis systems was deduced.

This was confirmed by subsequent pharmacological tests. A whole series of tests carried out on rats has shown that the new compounds exercise a considerable protective and resolutive action in hepatic steatosis by hyperlipidic-hyperproteic diet according to Handler, in steatosis by acute alcoholic intoxication and by other toxic agents (carbon tetrachloride, bromobenzene etc.) by the administration of only 6 mg/kg/i.p.; both from the morphohistochemical and analytical points of view, the SAM significantly reduces the accumulation of lipids at the hepatocite level while it favours the restoration of normal levels of phospholipids reduced after intoxication with $CCl_4$.

Hepatic phospholipids in rats after intoxication with $CCl_4$ and treatment with SAM.

| Treatment | Total phospholipids (mg/g) |
|---|---|
| Physiological solution | 30,57 ± 1,18 |
| $CCl_4$ | 18,87 ± 1,06 |
| $CCl_4$ + SAM 15 mg/kg/i.p. | 27,20 ± 1,25 |
| $CCl_4$ + SAM 150 mg/kg/i.p. | 20,87 ± 0,42 |
| $CCL_4$ + Ad + Met 15 mg/kg/i.p. | 19,9 ± 0,92 |

The values are the averages ± E.S. of 10 values for each group. In studying the hepatoprotective activity we have used an experimental device which produces in the rat the so-called hepatic cholesterol degeneration (Ridout and Coll., Biochem. J. 52, 99, 1952).

In this method, by means of a suitable diet, a conspicuous increase in the total hepatic fats and hepatic cholesterol are obtained in the animals. The substances which act in the lipidic metabolism reduce or annul this increase.

The animals were divided into six groups. The first group was administered with a diet which was varied at will. The second group was administered with the basic diet of Ridout (20 g per rat per day); the other groups were administered with the same diet in the same doses but enriched with cholesterol to the extent of 0.2 g/rat/day. The treatment lasted three weeks. The groups 4,5,6 were administered with SAM in the following doses:

0.4, 0.8, 2 mg/kg/i.p. per day.

At the end of the three weeks all the animals were killed, the livers were withdrawn and the total fats (Best and Coll., Biochem. J. 40, 368, 1966) and cholesterol (Sperry and Brand, J. Biol. Chem. 150, 315, 1943) were determined.

The results showed that the batches subjected to treatment with SAM in doses of 0.4–0.8 mg/kg/i.p. were poorly protected, while the batch treated with 2 mg/kg/i.p. was completely protected. Hepatic cholesterol and total fats at the end of the experiment (average per batch).

| Batch | Fresh liver weight g | Total fats g | Total fats % | Cholesterol mg | Cholesterol % |
|---|---|---|---|---|---|
| I | 15 | 1.41 | 9.4 | 40 | 2.6 |
| II | 18 | 1.93 | 10.6 | 68 | 3.7 |
| III | 16 | 3.84 | 24.0 | 92 | 5.7 |
| IV | 17 | 3.70 | 21.6 | 90 | 5.2 |
| V | 16 | 3.5 | 21.9 | 67 | 4.1 |
| VI | 16 | 2.0 | 12.5 | 61 | 3.8 |

Another pharmacological aspect investigated by us was the anti-inflammatory and analgesic effects of SAM.

Of the various tests we shall mention the most classic, namely the edema by carragenine and by egg white as a test for acute inflammation; and granuloma by cotton pellets and arthritis by adjuvant as a test for chronic inflammation. In all cases SAM proved active both administered orally (dose between 8 and 40 mg/kg) and parenterally (doses between 4 and 8 mg/kg) in comparison with other known drugs (Ibuprofen - Indometacina). The analgesia tests were in the form of the hot plate test and stretching by acetic acid, and the Randal and Selitto test in the rat. The drug also proved active in these tests in comparison with known drugs studied.

A further aspect considered by us was the possible action of SAM on the sleeping time by barbiturates.

For this purpose an experiment was carried out in which groups of mice received hexobarbital in a dose of 80 mg/kg/i.p. in accordance with the method of Holten and Larsen (Acta Pharmacol. Toxicol. 1956, 12, 346); one group was the control group and the second received SAM in a dose of 4 mg/kg/i.p. (table).

| Controls | Sleeping time (min.) |
|---|---|
|  | 24.4 ± 2.7 |
| SAM 4 mg/kg/i.p. | 41.2 ± 5.8 |

An examination of the data showed that SAM is active in prolonging the sleeping time induced by hexobarbital.

CLINICAL TESTS

Where the administration of SAM is mentioned hereinafter, this signifies the administration of any one of the salts according to the invention.

Following the information gained from the pharmacological tests, the clinical tests were orientated on morbid affections in which the following appear primarily or secondarily affected:

1 — the metabolism of lipids
2 — the metabolism of protids and glucids
3 — the metabolism of catecholamines and the biogene amines.

1. From tests conducted clinically on hundreds of subjects using doses of SAM varying over a very wide interval, it was found that the new compounds induce a rapid fall in the hepatic lipids in the hepatosteatosis of the most varied pathogenesis, identifiable by a bioptic examination repeated after the end of the treatment cycle, even after 60 days from the end of treatment.

The administration of the product also induces a marked fall in the high values of total cholesterolemia, of hypertriglyceridemia and normalises the altered $\beta/\alpha$ lipoproteic ratios in subjects with hyperdislipidemia in the uncompensated stage. This hypocholesterolemising and hypolipemising action is verified even in doses of about 8–1.5 mg administered 2–3 times per day, and is proportional to the dose.

In clear arteriosclerosis with clinical manifestations of the psycho-affective sphere, with turbemnesics and secondary centroencephalics (deterioration by arteriosclerotic encephalopathia) and phenomena of cerebral hypoxia, the administration of SAM by intermuscular or, in graver cases, by intravenous injection or by slow phleboclysis, in doses between 8 and 16 mg 3–4 times per day, has shown a very favourable modification of the symptomatology.

In particular, in clear hypoxydotic states the recovery of the functions concerned with the like of relationship was very quick and statistically significant.

In post-apoplectic syndromes a greater rapidity was found in the improvement of the clinical framework.

2. Hundreds of subjects were treated clinically affected with: secondary hypoprotidemias and disprotidemias; persistent and aggressive chronic hepatopathias; precyrrotic and cyrrotic states; malabsorption syndromes, and protide dispersing syndromes. The administration of doses variable between 20 and 80 mg of SAM per day by intermuscular or intravenous injection or orally, according to the gravity of the case, caused a statistically significant increase in the total protidemia, an increase in the albumin level and a tendency to normalise the altered percentage ratios betwen the electrophoretic fractions of the serum. This protein anabolising activity was followed by an often very important improvement in the subjective symptomology and the general objective conditions; and by the normalising of all the tests of hepatic functionality.

3. Particularly surprising results were obtained in clinical applications of the new enzymatic salt according to the invention, in which morbid frameworks existed which were clearly correlated with modifications in the exchange of biogene amines, for example:

a. pathological frameworks of neuropsychiatric pertinence;
b. Parkinsons disease and Parkinsonism of various eziopathogeneses;
c. Antiphologistic and analgesic action in the treatment of osteoarthritis, and antalgic activity in certain neurological manifestations;
d. disturbances of the sleeping-waking rhythm.

With regrad to point (a), a vast clinical casuistry conducted by examining the clinical behaviour and the tests of Hamilton and Wittenberg, has clearly shown that the administration of doses varying between 8 and 20 mg of SAM 3–4 times per day for a period of 5–15 days induces, excluding any other form of therapy, a significant remissione of the main parameters considered for the diagnosis of depressive forms.

With regard to point (b) relative to the treatment of Parkinsons disease and Parkinsonisms, it has been found that:

The administration of SAM in doses of 4–16 mg per day by intermuscular or intravenous injection, or orally - according to the gravity of the case - in association with the habitual therapy with Levodopa, gives rise to a statistically more significant improvement in the akinesia and rigidity in comparison with that which occurs in patients treated only with Levodopa.

Favourable modifications are also found in the extent of the Parkinson tremor, which cannot be modified by Levodopa alone.

The administration of SAM distinctly improves the Levodopa dependent psychic disturbances, with particular regard to depressive states and psychic manifestations of irritative type.

The administration of SAM in the aforementioned doses significantly blocks the train of Levodopa side effects of the various organs and apparatus, with particular regard to nausea, vomit, inappetite, hypotension, asthenia, cephalea, hypersudoration and insomnia.

With regard to point (c), SAM, which pharmacological results show to have intense antiphlofistic and analgesic activity, has proved active in all osteoarthritic forms treated with a dose of 13 mg twice a day by intermuscular or intravenous injection, and 13–20 mg orally 4 times per day.

After only 7 days of treatment, the muscular spasm, the limitation of movement, localised pain and rigidity were influenced in a statistically significant manner, with respect to the placebo.

No case of gastric pyrosis was observed in 90 cases treated. The search for concealed blood in the feces never showed any modification during the treatment.

SAM, compared with a non-steriod antiphlogistic drug commonly used in a double blind study, proved to possess a therapeutic efficiency equal to indomethacin.

The antalgic activity of SAM was also tested in different subjects with different neurological frameworks: neuritis, polyneuritis, anthralgia, sciatica, radiocolitis, torticollis.

The therapeutic effect was available and efficient from the first day of administration of a dose of 6 mg twice a day by intermuscular injection or 13–20 mg 3–4 times per day orally. Analogous results were obtained in subjects with recurring and resistant cephalalgia with the administration of the drug orally in masticable tablets.

With regard to point (d), i.e. disturbances of the sleeping-waking rhythm, with particular regard to insomnia, the new product according to the invention is able with a dose of 4–13 mg orally, to considerably improve the altered sleeping-waking ratios by inducing a physiological sleep without recurrence to the use of barbiturates or other substances of cortical and centroencephalic depressive action.

From that summarised heretofore the numerous unexpected perspectives opened up by the new drug in the field of human therapy are evident.

Summarising, we can say that the fields of use already ascertained are: treatment of hepatopias, hyperdislipidemias, generalised or local arteriosclerosis, psychiatric manifestations of depressive and neurological type, degenerative arthropathies, neurological algic manifestations and disturbances of the sleeping-waking rhythm, whereas many other fields of use still remain to be examined and ascertained.

The new SAM salts are preferably administered by intermuscular or intravenous injection, or in oral or sublingual tablets, or in capsules.

Some pharmaceutical compositions are given below:

| | | |
|---|---|---|
| a) | A 400 mg tablet contains | |
| | SAM | 28 mg |
| | Excipients: | |
| | Starch | |
| | Lactose | |
| | Magnesium stearate | |
| | Talc | |
| | Aroma | q.n. to 400 mg |
| b) | A 250 mg capsule contains | |
| | SAM | 28 mg |
| | Excipients: | |
| | Starch | |
| | Lactose | |
| | Magnesium stearate | |
| | $Na_3PO_4$ | q.n. to 250 mg |
| c) | A lyophilised phial contains | |
| | SAM | 4.6 mg |
| | A muscular solvent phial contains | |
| | Lidocaine | 20 mg |
| | Solution of phosphate buffers | q.n. to 3 ml |
| d) | A lyophilised phial contains | |
| | SAM | 14 mg |
| | A muscular solvent phial contains | |
| | Lidocaine | 20 mg |
| | Solution of phosphate buffers | q.n. to 3 ml |
| e) | A 2 g suppository contains | |
| | SAM | 46.6 mg |
| | Suppository mass | q.n. to 2.0 g |

Other forms of administration may be:
a. Drinkable liquids
b. Liquids for ocular instillation
c. Liquids for intranasal instillation
d. Liquids for aerosol or spray application
e. Liquids and ointments for topical use in which the active principle is diluted in the normal acceptable pharmaceutical solvents ("Tecnologia Farmaceutica" - Second Volume, Silvano Casadio, Second Edition — ed. Cisalpino-Goliardica — Milan, 1972).

In conclusion we may say that the therapeutic doses of SAM lie between 2 and 125 mg per day, according to the particular type and gravity of the affection treated.

Larger doses may be used if necessary in view of the absolute absence of toxicity of the salts according to the invention.

I claim:

1. Stable salts of S-adenosil-L-methionine (SAM) with sulphonic acids selected from the group consisting of methanesulphonic, ethanesulphonic, 1-n-dodecanesulphonic, 1-n-octadecanesulphonic, 2-chloroethanesulphonic, 2-bromoethanesulphonic, 2-hydroxyethanesulphonic, 3-hydroxypropanesulphonic, d-,1-,d,1-10-camphorsulphonic, d-,1-,d,1-3-bromocamphor-10-sulphonic, cysteic, benzenesulphonic, p-chlorobenzenesulphonic, 2-mesitylbenzenesulphonic, 4-biphenylsulphonic, 1-naphthalenesulphonic, 2-naphthalenesulphonic, 5-sulphosalicylic, p-acetylbenzenesulphonic, 1,2-ethanedisulphonic, o-benzenedisulphonic and chondroitinesulphuric acids, and double salts of said acids with sulphuric acid.

2. A stable salt according to claim 1 selected from the group consisting of the S-adenosil-L-methionine (SAM) salt of methanesulphonic acid and the double salt of said acid with sulphuric acid.

3. A stable salt according to claim 1 selected from the group consisting of the S-adenosil-L-methionine (SAM)

salt of ethanesulphonic acid and the double salt of said acid with sulphuric acid.

4. A stable salt according to claim 1 selected from the group consisting of the S-adenosil-L-methionine (SAM) salt of 1-n-dodecanesulphonic acid and the double salt of said acid with sulphuric acid.

5. A stable salt according to claim 1 selected from the group consisting of the S-adenosil-L-methionine (SAM) salt of 1-n-octadecanesulphonic acid and the double salt of said acid with sulphuric acid.

6. A stable salt according to claim 1 selected from the group consisting of the S-adenosil-L-methionine (SAM) salt of 2-chloroethanesulphonic acid and the double salt of said acid with sulphuric acid.

7. A stable salt according to claim 1 selected from the group consisting of the S-adenosil-L-methionine (SAM) salt of 2-bromoethanesulphonic acid and the double salt of said acid with sulphuric acid.

8. A stable salt according to claim 1 selected from the group consisting of the S-adenosil-L-methionine (SAM) salt of 2-hydroxyethanesulphonic acid and the double salt of said acid with sulphuric acid.

9. A stable salt according to claim 1 selected from the group consisting of the S-adenosil-L-methionine (SAM) salt of 3-hydroxypropanesulphonic acid and the double salt of said acid with sulphuric acid.

10. A stable salt according to claim 1 selected from the group consisting of the S-adenosil-L-methionine (SAM) salt of d-,l-,d,l-10-camphorsulphonic acid and the double salt of said acid with sulphuric acid.

11. A stable salt according to claim 1 selected from the group consisting of the S-adenosil-L-methionine (SAM) salt of d-,l-,d,l-3-bromocamphor-10-sulphonic acid and the double salt of said acid with sulphuric acid.

12. A stable salt according to claim 1 selected from the group consisting of the S-adenosil-L-methionine (SAM) salt of cysteic acid and the double salt of said acid with sulphuric acid.

13. A stable salt according to claim 1 selected from the group consisting of the S-adenosil-L-methionine (SAM) salt of benzenesulphonic acid and the double salt of said acid with sulphuric acid.

14. A stable salt according to claim 1 selected from the group consisting of the S-adenosil-L-methionine (SAM) salt of p-chlorobenzenesulphonic acid and the double salt of said acid with sulphuric acid.

15. A stable salt according to claim 1 selected from the group consisting of the S-adenosil-L-methionine (SAM) salt of 2-mesitylbenzenesulphonic acid and the double salt of said acid with sulphuric acid.

16. A stable salt according to claim 1 selected from the group consisting of the S-adenosil-L-methionine (SAM) salt of 4-biphenylsulphonic acid and the double salt of said acid with sulphuric acid.

17. A stable salt according to claim 1 selected from the group consisting of the S-adenosil-L-methionine (SAM) salt of 1-naphthalenesulphonic acid and the double salt of said acid with sulphuric acid.

18. A stable salt according to claim 1 selected from the group consisting of the S-adenosil-L-methionine (SAM) salt of 2-naphthalenesulphonic acid and the double salt of said acid with sulphuric acid.

19. A stable salt according to claim 1 selected from the group consisting of the S-adenosil-L-methionine (SAM) salt of 5-sulphosalicylic acid and the double salt of said acid with sulphuric acid.

20. A stable salt according to claim 1 selected from the group consisting of the S-adenosil-L-methionine (SAM) salt of p-acetylbenzenesulphonic acid and the double salt of said acid with sulphuric acid.

21. A stable salt according to claim 1 selected from the group consisting of the S-adenosil-L-methionine (SAM) salt of 1,2-ethanedisulphonic acid and the double salt of said acid with sulphuric acid.

22. A stable salt according to claim 1 selected from the group consisting of the S-adenosil-L-methionine (SAM) salt of o-benzenedisulphonic acid and the double salt of said acid with sulphuric acid.

23. A stable salt according to claim 1 selected from the group consisting of the S-adenosil-L-methionine (SAM) salt of chondroitinesulphuric acid and the double salt of said acid with sulphuric acid.

* * * * *